US011253331B2

(12) United States Patent
Grenier

(10) Patent No.: US 11,253,331 B2
(45) Date of Patent: Feb. 22, 2022

(54) PROTECTIVE COVERING FOR PREEXISTING AFFIXED MEDICAL EQUIPMENT SAFETY STRAPS

(71) Applicant: Melissa Marie Grenier, Baldwin Park, CA (US)

(72) Inventor: Melissa Marie Grenier, Baldwin Park, CA (US)

(*) Notice: Subject to any disclaimer, the term of this patent is extended or adjusted under 35 U.S.C. 154(b) by 668 days.

(21) Appl. No.: 15/581,371

(22) Filed: Apr. 28, 2017

(65) Prior Publication Data
US 2017/0258542 A1    Sep. 14, 2017

Related U.S. Application Data

(63) Continuation of application No. 14/200,413, filed on Mar. 7, 2014, now abandoned, which is a
(Continued)

(51) Int. Cl.
*A61B 46/10* (2016.01)
*A61F 5/37* (2006.01)
(Continued)

(52) U.S. Cl.
CPC ............... *A61B 46/10* (2016.02); *A61B 50/00* (2016.02); *A61F 5/3776* (2013.01); *A61G 13/10* (2013.01); *A61B 2050/0085* (2016.02)

(58) Field of Classification Search
CPC ..... A61B 5/02233; A61B 46/00; A61B 46/10; A61B 46/23; A61B 50/00; A61B 2050/005; A61B 2050/0065; A61B 2050/0085; A61B 46/27; A61B 2046/234; A61B 2050/314; A61B 2050/3008; A61B 2050/3009; A61B 2050/3014; A61B 2050/3015; A61F 5/02; A61F 5/028; A61F 5/03; A61F 5/37; A61F 5/3715; A61F 5/3761; A61F 5/3769; A61F 5/3776; A61F 5/3792; A61F 5/40; A61F 5/0584; A61F 5/0585; A61F 5/05858; A61F 5/05866; A61F 5/0504; A61F 15/007; A61F 15/02; A61G 1/044; A61G 7/0507;
(Continued)

(56) References Cited

U.S. PATENT DOCUMENTS 5,251,646 A * 10/1993 Bowen ............... A61B 5/02233
128/878
5,465,425 A * 11/1995 Crispin ............... A41D 13/0012
2/102
(Continued)

*Primary Examiner* — Keri J Nelson
*Assistant Examiner* — Adam Baker
(74) *Attorney, Agent, or Firm* — Averill & Green; Kenneth L Green

(57) ABSTRACT

A disposable cover used to protect preexisting affixed safety straps on medical equipment. The cover includes: 2 protective panels and hook and loop fasteners on the inside for securing the cover to the preexisting affixed strap and hook and loop fasteners on the outer surface to allow the cover to secure to the opposing cover. This disposable protective cover is slipped over the preexisting affixed safety straps that are attached to the medical equipment prior to being used to
(Continued)

secure a patients' body/limb to the medical equipment for a procedure, allowing the strap to be protected from infectious fluids.

20 Claims, 5 Drawing Sheets

Related U.S. Application Data continuation of application No. 13/573,175, filed on Aug. 24, 2012, now abandoned, which is a continuation of application No. 13/485,833, filed on May 31, 2012, now abandoned.

(60) Provisional application No. 61/620,311, filed on Apr. 4, 2012.

(51) Int. Cl.
*A61B 50/00* (2016.01)
*A61G 13/10* (2006.01)

(58) Field of Classification Search
CPC ........ A61G 13/10; A61G 7/065; A61G 7/075; A61G 7/1082; A61G 7/1092; A61G 7/1094; A61G 7/0504; A61G 13/12; A61G 13/124; A61G 13/122; A61G 13/1235; A61G 13/1245; A61G 1/01; A41F 15/00; A41F 15/02; A41F 15/007; A61M 2025/0246; F16G 11/02; B60R 22/10; B60R 22/105; B60R 22/14; B60R 22/30; B60R 22/00; B60R 22/001; B60R 22/12; B60R 2022/006; B60R 2022/003; B60R 2022/008; B60N 2/2815; B60N 2/2881; B60N 2/2812; A41D 13/0007; A41D 13/046; A41D 13/086; A41D 13/08; A41D 15/005; A41D 15/02; A61H 3/008; A61H 2201/1652; A61H 2201/0162; A61H 2201/1621; A61H 31/00; A61H 31/006; A61H 31/007; A62B 35/00; A47G 9/0253; A47G 9/0261
USPC ................ 128/849, 852, 856, 878; 604/263; 248/309.1
See application file for complete search history.

(56) References Cited

U.S. PATENT DOCUMENTS

| | | | | |
|---|---|---|---|---|
| 5,676,095 A | * | 10/1997 | Ralls | ..................... A01K 13/007 |
| | | | | 119/850 |
| 6,079,049 A | * | 6/2000 | Moir | .................. A41D 19/0027 |
| | | | | 2/108 |
| 7,011,615 B2 | * | 3/2006 | Price | ....................... B65D 31/12 |
| | | | | 383/41 |
| 7,708,720 B1 | * | 5/2010 | Angstrom | ............. A61M 25/02 |
| | | | | 604/263 |
| 2002/0078536 A1 | * | 6/2002 | Martin | .................. A61F 13/622 |
| | | | | 24/450 |
| 2005/0061330 A1 | * | 3/2005 | Fenwick | ................ A61B 46/23 |
| | | | | 128/849 |
| 2005/0087196 A1 | * | 4/2005 | Deem-Rockstroh | ..... A61G 1/01 |
| | | | | 128/869 |
| 2005/0211590 A1 | * | 9/2005 | McClure | ................ A61B 46/10 |
| | | | | 206/438 |
| 2007/0124899 A1 | * | 6/2007 | Israel | ................. A44B 18/0084 |
| | | | | 24/306 |
| 2007/0163419 A1 | * | 7/2007 | Montgomery | ......... G10G 5/005 |
| | | | | 84/327 |
| 2007/0267026 A1 | * | 11/2007 | Grant-Jennings | ...... A61B 50/30 |
| | | | | 128/846 |
| 2009/0264709 A1 | * | 10/2009 | Blurton | ................. A61F 5/3784 |
| | | | | 600/206 |
| 2010/0236287 A1 | * | 9/2010 | Summerford | ........ A44C 15/005 |
| | | | | 63/1.12 |
| 2012/0266899 A1 | * | 10/2012 | Goldsmith | ............ A61F 5/3776 |
| | | | | 128/876 |
| 2013/0042386 A1 | * | 2/2013 | Montgomery | ........ A61F 5/3792 |
| | | | | 2/102 |

\* cited by examiner

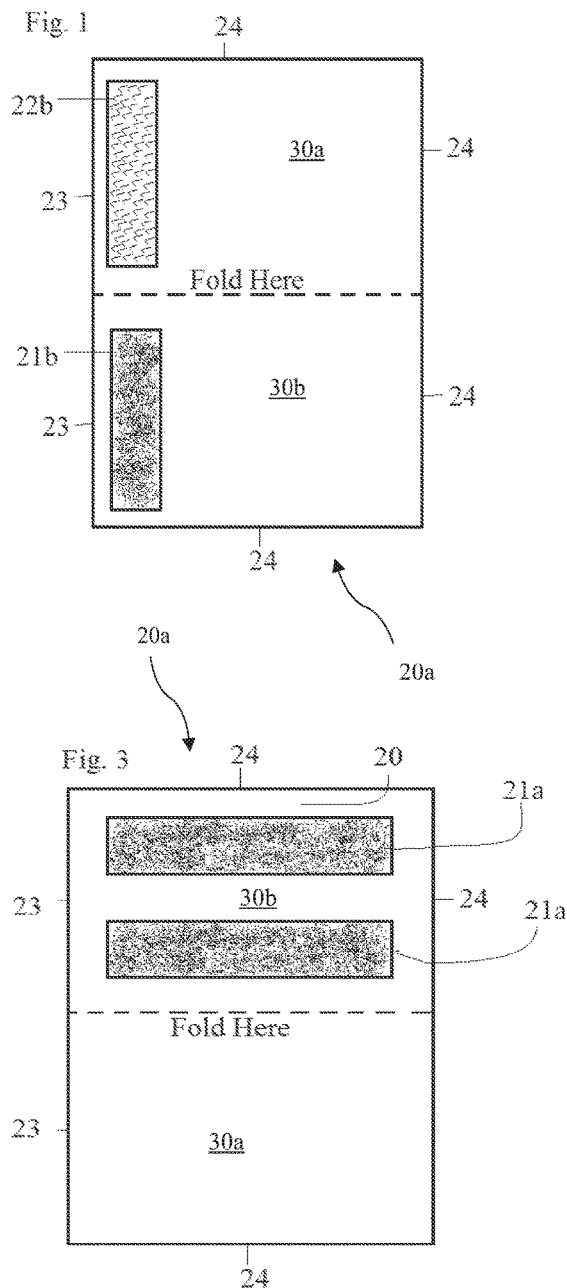
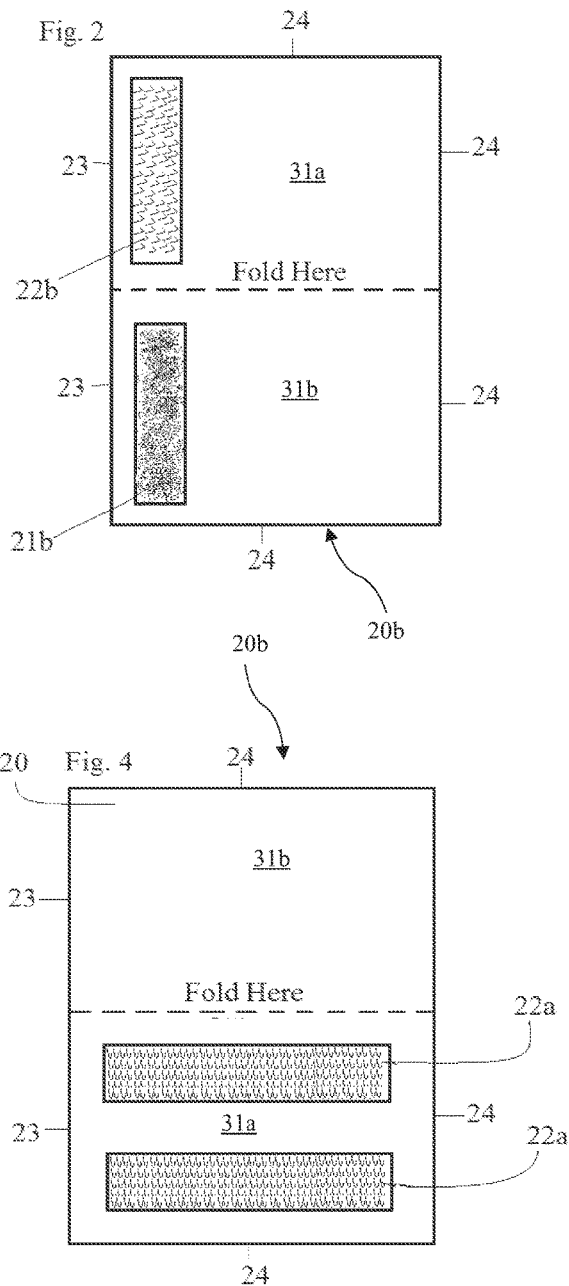

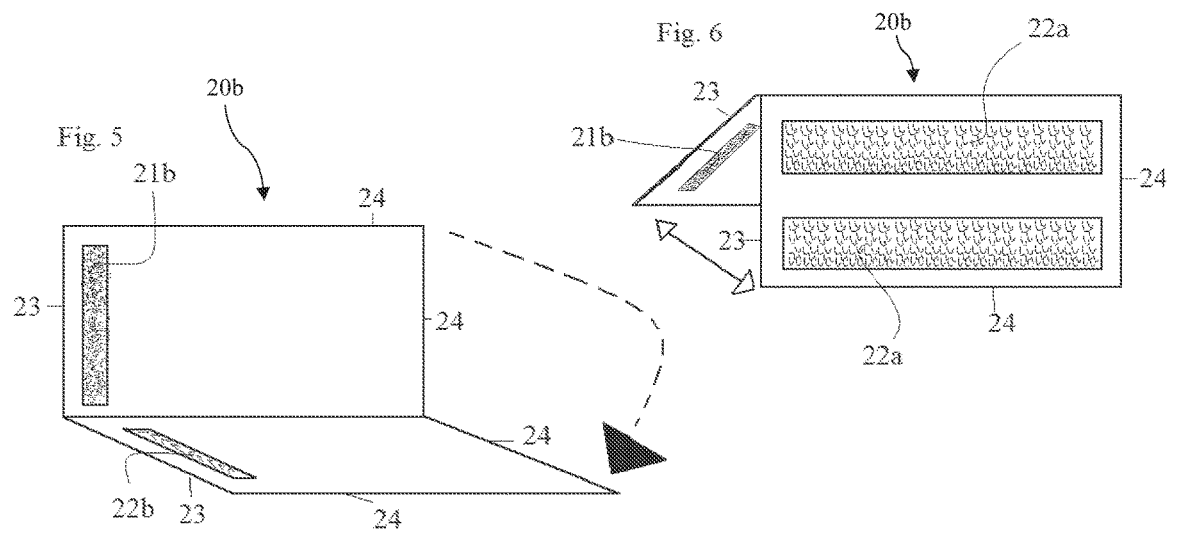
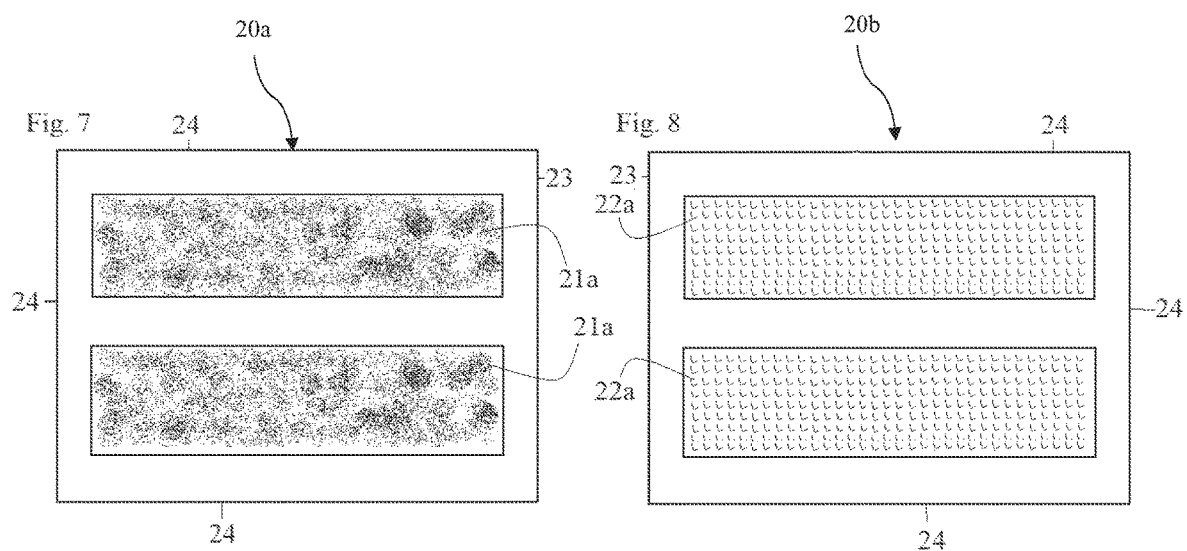

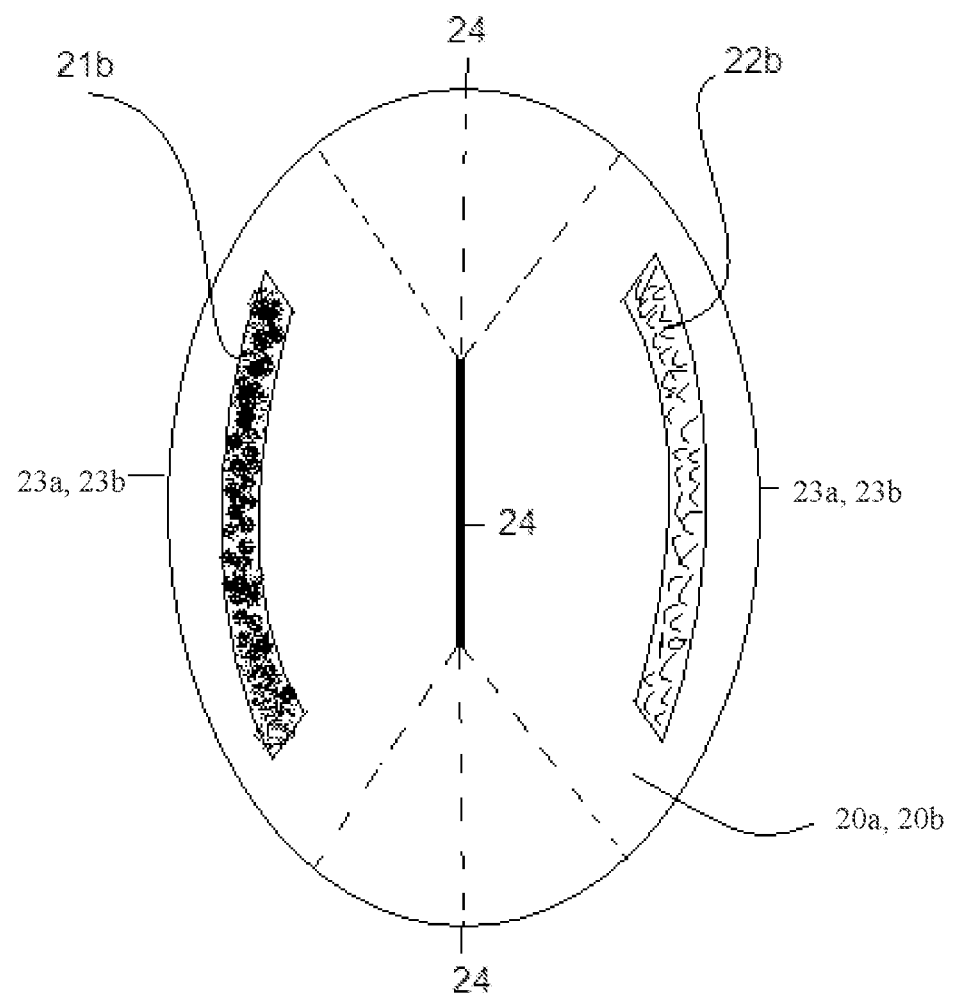

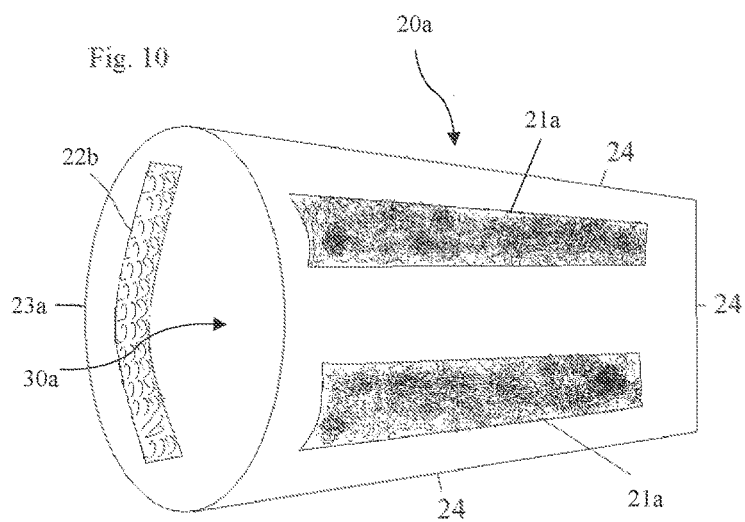
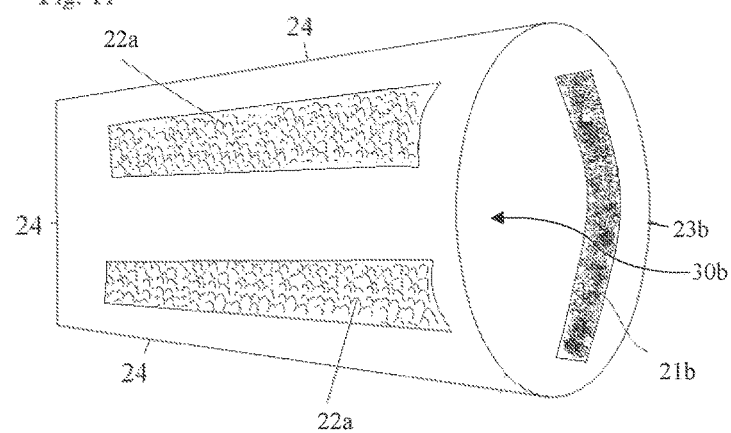

PROTECTIVE COVERING FOR PREEXISTING AFFIXED MEDICAL EQUIPMENT SAFETY STRAPS

The present application is a continuation in part of the U.S. non-utility patent application Ser. No. 14/200,413 dated Mar. 7, 2014 entitled: Protective covering for medical equipment safety straps, which will become May 7, 2017 and continuation of the U.S. non-utility patent application Ser. No. 13/573,175 dated Aug. 24, 2012 entitled: Protective covering for medical equipment safety straps, which will become Mar. 9, 2014 and a continuation of the U.S. non-utility patent application Ser. No. 13/485,833 dated May 31, 2012 entitled: Protective covering for medical equipment safety straps, which claims priority to U.S. provisional patent application No. 61/620,311 dated Apr. 4, 2012 entitled: Protective covering for medical equipment safety straps each of which is incorporated herein by reference in its entirety.

CROSS-REFERENCE TO RELATED APPLICATIONS

This application claims priority to U.S. provisional patent application No. 61/620,311 filed Apr. 4, 2012, is a continuation of U.S. patent application Ser. No. 13/485,833 filed May 31, 2012, is a continuation of U.S. patent application Ser. No. 13/573,175 filed Aug. 24, 2012, and is continuation of U.S. patent application Ser. No. 14/200,413 filed Mar. 7, 2014, the subject matter of which are incorporated herein by reference in their entirety.

STATEMENT REGARDING FEDERALLY SPONSORED RESEARCH OR DEVELOPMENT

Not Applicable

THE NAMES OF THE PARTIES TO JOINT RESEARCH AGREEMENT

Not Applicable

BACKGROUND

Preexisting affixed safety straps on medical equipment and/or procedural tables are used in a variety of medical settings i.e. CT scan tables, MRI tables, Cardiac Cath Lab tables and GI procedure tables. Medical personnel must use straps to secure patients/limbs to the table so that the patient does not fall off and incur further injury. Although effective, one commonly over looked risk is the multiple uses of these preexisting affixed safety straps after being contaminated with communicable diseases by infected patients. Currently these straps are not being disinfected and/or cleaned regularly due to the time constraints, even when there is a clear contamination of infectious fluids. This increases the patients risk of being exposed to other infections not related to their current stay, and could possibly become detrimental to the patients health if the patients immune system is compromised. Health Care-Associated Infections (HAI) increase a facilities outward cost. Approximately 2 million patients each year in the United States alone are affected by HAI's. This staggering number results in an estimated 90,000 deaths and an estimated $4.5-$5.7 billion dollars per year in additional health related costs to facilities for extended health care and/or death related lawsuits. Although it is nearly impossible to pinpoint where an infection origin's derived from, it is the facilities duty/responsibility to ensure that the patient environment is a clean and contaminate free to the best of their ability.

SUMMARY

The present invention addresses the problem of transmission of infectious contaminates from person to person when the preexisting affixed medical safety straps are used. Preexisting affixed medical safety straps are used hundreds of times a day but not regularly cleaned which can have an adverse effect if the patient comes into contact with the infected fluid. Medical personal attempt to disinfect the preexisting affixed safety straps by using an anti-microbial cleaner and/or laundering when they believe the straps have been contaminated. This takes up valuable time and is not always effective. An embodiment of the invention is a protective covering made of flexible impermeable material with a series of hook-and-loop fasteners. This is a preferred method of limiting the introduction of infectious fluids or skin contact with preexisting affixed safety straps.

An embodiment of the invention is a method of protecting a patient from HAI's by reducing the exposure to possible contaminates previously left behind on infected preexisting affixed medical safety straps while maintaining the integrity (security) of the safety strap.

DESCRIPTION OF DRAWINGS

FIG. 1 depicts an inside open view of the cover to show hook-and-loop placement.

FIG. 2 depicts an inside open view of the cover to show hook-and-loop placement.

FIG. 3 depicts an outside open view of the cover to show the placement of the loop side fastener.

FIG. 4 depicts an outside open view of the cover to show the placement of the hook side fastener.

FIG. 5 depicts the assembly of the cover whereby two sides are sealed.

FIG. 6 depicts the assembly of the cover whereby two sides are sealed.

FIG. 7 depicts the outside view of finished safety strap cover.

FIG. 8 depicts the outside view of finished safety strap cover.

FIG. 9 depicts the inside view of the cover to display the placements of the hook-and-loop fasteners.

FIG. 10 depicts the relationship of the inside hook-and-loop fasteners to the hook-and-loop fasteners of the outside of the cover.

FIG. 11 depicts the relationship of the inside hook-and-loop fasteners to the hook-and-loop fasteners of the outside of the cover.

DRAWING REFERENCE NUMBERS

Figure 12:
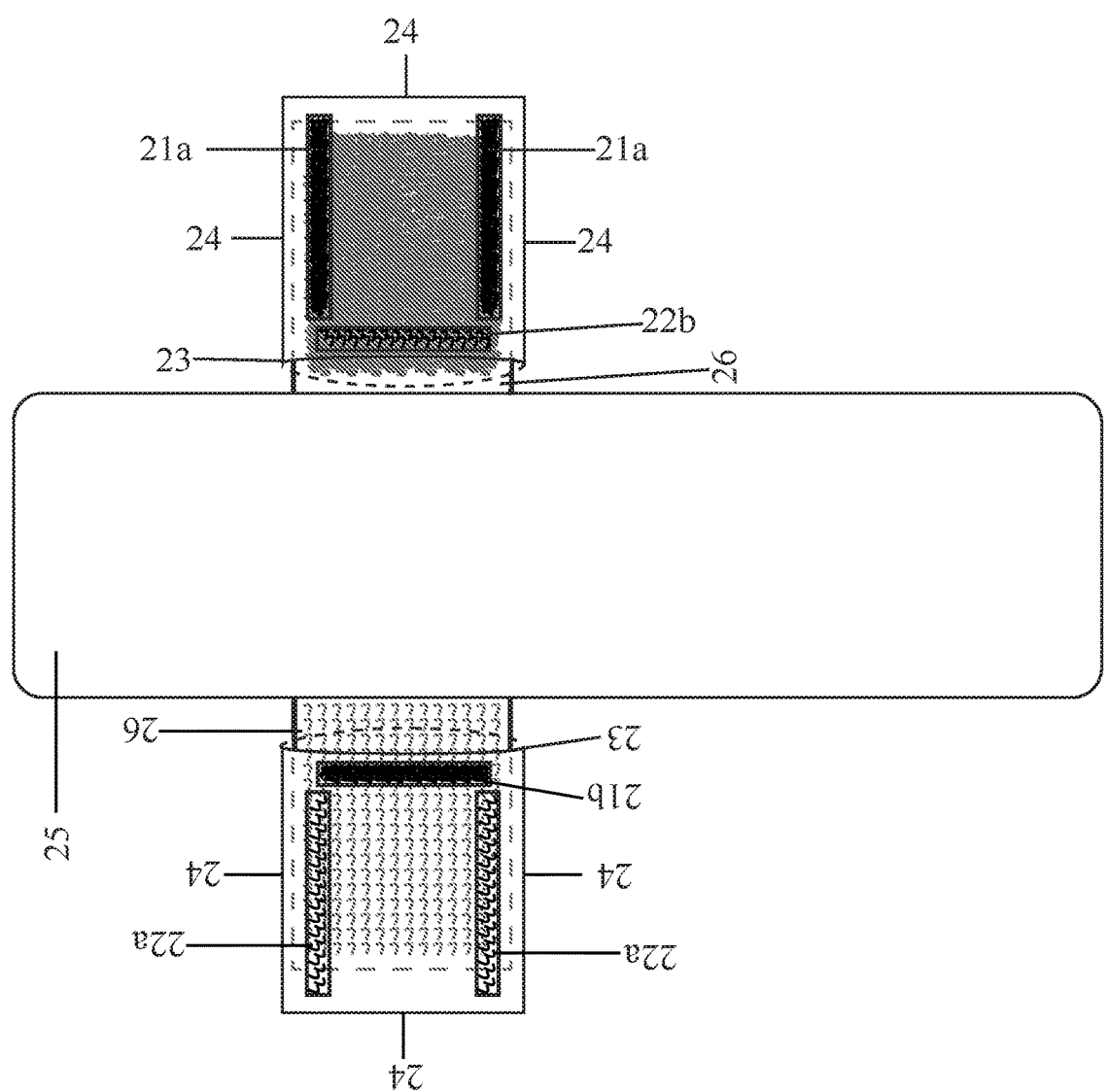
FIG. 12 depicts how the protective covers are placed onto the preexisting affixed safety straps.

20 Protective cover
21a Loop fastener (outside cover)
21b Loop fastener (inside open end)
22a Hook fastener (outside cover)
22b Hook fastener (inside open end)
23a First open end 23b Second open end
24 Sealed edges
25 Procedure Table
26 Procedure Table preexisting affixed safety strap

DETAILED DESCRIPTION

One embodiment of the protective cover is illustrated in FIG. 1 and FIG. 2 inside view. The protective cover is the open view of the covers 20a and 20b with the placement of the inside hook-and-loop fasteners 21b and 22b on first side 30a, second side 30b, third side 31a. and fourth side 31b. The protective cover consists of any material impermeable to fluids the preferred embodiment of the material is plastic. The protective covers 20a and 20b can be cut into various sizes to accommodate the varies sizes of the preexisting affixed safety straps. At the open ends 23a and 23b of the protective covers 20a and 20b respectively the hook-and-loop fasteners 21b and 22b are placed for fastening opposed edge portions of the safety strap. The other three edges 24 will be closed to seal the protective cover.

FIGS. 3 and 4 depicts a view of the outside of the protective cover. This view depicts the outside embodiment of the protective covers 20a and 20b and placement of hook-and-loop fasteners 21a and 22a before the ends are sealed 24.

FIG. 5 depicts the inside embodiment of the protective cover in the process of being sealed 24 to depict what will be the inside of the protective cover. The hook-and-loop fasteners 21b and 22b of the inside will adhere to the preexisting affixed safety straps.

FIG. 6 depicts the outside embodiment of the protective cover in the process of being sealed 24 to depict what will be the outside of the protective cover with the hook or loop fastener 22a which will allow the protective covers to fasten to each other. It also depicts the placement of the inside hook-and-loop fastener 21b in accordance to the placement of the outside hook-and-loop fastener 22a before the protective cover is sealed on three sides 24.

FIGS. 7 and 8 depicts the outside embodiment of each protective cover once the three sides 24 are sealed. It shows the placement of the hook and loop fasteners 21a and 22a on the outside embodiment of the protective covers and how they intend to adhere to one another.

FIG. 9 depicts to embodiment of an open view of the protective cover after being sealed 24 displaying the placement of the inside hook-and-loop fasteners 21b and 22b in accordance with the placement to the open ends 23a and 23b.

FIGS. 10 and 11 depicts a finished set of protective covers with the placement of the hook-and-loop fasteners 21b and 22b in inside of the open ends 23a and 23b that will adhere to the preexisting affixed safety strap, as well as on the hook-and loop fasteners 21a and 22a on the outside that w ill adhere to adjacent protective cover.

FIG. 12 depicts the protective covers and how they are placed onto to the preexisting affixed safety strap. Once the protective cover is slipped over the safety strap, the hook-and-loop fasteners on the protective cover 21b fasten to the opposed hook-and-look fasteners 26 on the preexisting affixed safety strap which are attached to the medical table 25. Once the protective covers 20a and 20b are fastened into place using the hook-and-loop fasteners 21b to the opposed preexisting affixed safety straps hook-and-loop fasteners 26 allowing the covered protected preexisting affixed safety straps to be wrapped around the patients' body/limb and securing the patient to the medical table 25.

The invention claimed is:

1. A pair of cooperating disposable protective covers for medical table affixed safety straps, comprising:
    a first cover comprising:
        a first open end of a first passage configured to slide over a first free safety strap end of a first affixed safety strap, the first free safety strap end opposite to a first affixed safety strap end attached to medical equipment or tables, the first cover providing a first clean outside surface for contact with a patient to prevent or reduce the likelihood of the patient acquiring a Health Care-Associated Infection (HAI);
        a first inside surface of the first cover facing in and a first outside surface of the first cover facing out, the first inside surface opposite to the first outside surface;
        first hook-and-loop fasteners on the first inside surface selected to engage second hook-and-loop fasteners on the first free safety strap end of the first affixed safety strap; and
        third hook-and-loop fasteners on the first outside surface; and
    a second cover attachable to and detachable from the first cover, the second cover comprising:
        a second open end of a second passage configured to slide over a second free safety strap end of a second affixed safety strap, the second free safety strap end opposite to a second affixed safety strap end attached to the medical equipment or tables, the second cover providing a second clean outside surface for contact with the patient to prevent or reduce the likelihood of the patient acquiring the HAI;
        a second inside surface of the second cover facing in and a second outside surface of the second cover facing out, the second inside surface opposite to the second outside surface;
        fourth hook-and-loop fasteners on the second inside surface selected to engage fifth hook-and-loop fasteners on the second free safety strap end of the second affixed safety strap; and
        sixth hook-and-loop fasteners on the second outside surface configured to engage the third hook-and-loop fasteners on the first outside surface to directly intimately attach the second cover to the first cover positioning the first and second covers overlapping and the first open end opposite to the second open end;
    wherein:
    the first affixed safety strap and the second affixed safety strap are attached to medical equipment and/or procedural tables;
    the first hook-and-loop fasteners are attached to the second hook-and-loop fasteners on the first free safety strap end of the first affixed safety strap;
    the fourth hook-and-loop fasteners are attached to the fifth hook-and-loop fasteners of the second free safety strap end of the second affixed safety strap;
    the first and second free safety strap ends including the second hook-and-loop fasteners and the fifth hook-and-loop fasteners respectively and configured to intimately connect over a patient or patient limb when uncovered to secure the patient or the patient limb to the medical equipment or table; and
    the third hook-and-loop fasteners configured to engage the sixth hook-and-loop fasteners to directly intimately attach the first cover to the second cover to secure the patient or the patient limb to the medical equipment or table: the covers are made of an impermeable material limiting intimate patient skin contact with the affixed safety straps and limiting the introduction of infectious fluids to the patient to prevent or reduce the likelihood of the patient acquiring the HAI.

2. The covers of claim 1, wherein:
the first hook and loop fasteners are attached to the first cover proximal to the first open end; and
the fourth hook and loop fasteners are attached to the second cover proximal to the second open end.

3. The covers of claim 1, wherein:
the first cover is closed on first opposite sides and on a third end opposite to the first open end and the first hook and loop fasteners are attached to the first cover proximal to the first open end; and
the second cover is closed on second opposite sides and on a fourth end opposite to the second open end and the fourth hook and loop fasteners are attached to the second cover proximal to the second open end.

4. The covers of claim 1, wherein the covers are separate when not attached by the third and sixth hook and loop material.

5. The covers of claim 1, wherein:
either:
the first hook and loop fasteners are first hoop fasteners and the fourth hook and loop fasteners are fourth loop fasteners; or
the first hook and loop fasteners are first loop fasteners and the fourth hook and loop fasteners are fourth hook fasteners; and
either:
the third hook and loop fasteners are third loop fasteners and the sixth hook and loop fasteners are sixth hook fasteners; or
the third hook and loop fasteners are third hook fasteners and the sixth hook and loop fasteners are sixth hook fasteners.

6. The covers of claim 1, wherein:
the first hook and loop fasteners are first hook fasteners and first cooperating loop fasteners resides on the first inside surface facing the first hoop fasteners;
the fourth hook and loop fasteners are fourth loop fasteners and fourth cooperating hook fasteners resides on the second inside surface facing the fourth loop fasteners;
the third hook and loop fasteners are third loop fasteners; and
the sixth hook and loop fasteners are sixth hook fasteners.

7. The covers of claim 1, wherein the first cover is positionable to totally overlap the second cover when the first and second covers are attached by the third and sixth hook-and-loop fasteners.

8. The covers of claim 1, wherein:
the third hook-and-loop fasteners extend most of the length between the first open end and a first closed end opposite to the first open end; and
the sixth hook-and-loop fasteners extend most of the length between the second open end and a second closed end opposite to the second open end.

9. The covers of claim 1, wherein a first position of the first hook-and-loop fasteners on the first inside surface of the first cover to engage the second hook-and-loop fasteners on the first free safety strap end of the first affixed safety strap, and a second position of the fourth hook-and-loop fasteners on the second inside surface of the second cover to engage the fifth hook-and-loop fasteners on the second free safety strap end of the second affixed safety strap, positions the third hook-and-loop fasteners on the first cover to engage the sixth hook-and-loop fasteners on the second cover.

10. The covers of claim 1, wherein the medical equipment and/or procedural tables are selected from the group consisting of CT scan tables, MRI tables, Cardiac Cath Lab tables and GI procedure tables.

11. A pair of cooperating disposable protective covers for medical table affixed safety straps, comprising:
a first disposable cover having a first inside surface and a first outside surface, and made from an impermeable material and comprising:
a first open end, closed first sides, a first closed end opposite to the first open end, and configured to slide over a first free safety strap end of a first affixed safety strap, generally covering the first free safety strap end and reaching proximal to medical equipment or tables the first affixed safety strap is affixed to, the first cover having an interior width proximal to a width of the first free safety strap end and wider than the first affixed safety strap, the first free safety strap end opposite to a first affixed safety strap end attached to the medical equipment or tables;
first hook-and-loop fasteners on the first inside surface selected to engage second hook-and-loop fasteners on the first free safety strap end of the first affixed safety strap; and
third hook-and-loop fasteners on the first outside surface; and
a second disposable cover having a second inside surface and a second outside surface, and made from the impermeable material and comprising:
a second open end, closed second sides, a second closed end opposite to the first open end, and configured to slide over a second free safety strap end of a second affixed safety strap, generally covering the second free safety strap end and reaching proximal to medical equipment or tables the second affixed safety strap is affixed to, the second cover having an interior width proximal to a width of the second free safety strap end and wider than the second affixed safety strap, the second free safety strap end opposite to a second affixed safety strap end attached to the medical equipment or tables;
fourth hook-and-loop fasteners on the second inside surface selected to engage fifth hook-and-loop fasteners on the second safety strap end of the second safety strap, wherein the fifth hook-and-loop fasteners are configured to engage the second hook-an-loop fasteners; and
sixth hook-and-loop fasteners on the second outside surface configured to directly engage the third hook-and-loop fasteners to attach the second cover to the first cover, positioning the first and second covers overlapping and the first open end opposite to the second open end, wherein either the sixth hook-and-loop fasteners is a hook fastener and the third hook-and-loop fasteners is a loop fastener, or the sixth hook-and-loop fasteners is a loop fastener and the third hook-and-loop fasteners is a hook fastener,
wherein:
the first cover providing a first clean outside surface for contact with a patient to prevent or reduce the likelihood of the patient acquiring a Health Care-Associated Infection (HAI);

the second cover providing a second clean outside surface for contact with the patient to prevent or reduce the likelihood of the patient acquiring the HAI; and the covers are made of the impermeable material limiting intimate patient skin contact with the affixed safety straps and limiting the introduction of infectious fluids to the patient to prevent or reduce the likelihood of the patient acquiring the HAI.

12. The covers of claim 11, wherein the first cover is positionable to totally overlap the second cover when the first and second covers are attached by the third and loop fasteners and the sixth hook fasteners.

13. The covers of claim 11, wherein when the first hook-and-loop fasteners engage the first affixed safety strap and the fourth hook-and-loop fasteners engage the second affixed safety strap, the third hook-and-loop fasteners face the sixth hook-and-loop fasteners.

14. The covers of claim 11, wherein:
the third hook-and-loop fasteners extend most of the length between the first open end and the first closed end; and
the sixth hook-and-loop fasteners extend most of the length between the second open end and the second closed end.

15. The covers of claim 11, wherein the covers are separate when not attached by the third and sixth hook and loop material.

16. A pair of cooperating disposable protective covers for medical table affixed safety straps, comprising:
a first cover comprising:
closed on three first edges, and having a first open end of a first passage into the first cover configured to slide over a first free safety strap end of a first affixed safety strap, the first free safety strap end opposite to a first affixed safety strap end attached to medical equipment or tables;
first hook fasteners on a first inside surface of the first cover, proximal to the first open end;
first loop fasteners on a second inside surface of the first cover facing the first inside surface, proximal to the first open end; and
third hook-and-loop fasteners on a first outside surface of the first cover; and
a second cover comprising:
closed on three second edges and having a second open end of a second passage into the second cover configured to slide over a second free safety strap end of a second affixed safety strap, the second free safety strap end opposite to a second affixed safety strap end attached to the medical equipment or tables;
fourth hook fasteners on a third inside surface of the second cover;
fourth loop fasteners on a fourth inside surface of the fourth side of the second cover facing the third inside surface, proximal to the second open end; and
sixth hook and loop fasteners on a second outside surface of the second cover configured to engage the third hook-and-loop fasteners to directly intimately attach the second cover to the first cover positioning the first cover overlapping the second cover and the first open end facing opposite to the second open end,
wherein:
the first free safety strap end resided between the first inside surface of the first cover and the second inside surface of the first cover, the first free safety strap end separating the first hook fasteners from the first loop fasteners; and
the second free safety strap end resided between the third inside surface of the second cover and the fourth side of the second cover, the second free safety strap end separating the fourth hook fasteners from the fourth loop fasteners,
wherein:
the first cover providing a first clean outside surface for contact with a patient to prevent or reduce the likelihood of the patient acquiring a Health Care-Associated Infection (HAI);
the second cover providing a second clean outside surface for contact with the patient to prevent or reduce the likelihood of the patient acquiring the HAI; and
the covers are made of the impermeable material limiting intimate patient skin contact with the affixed safety straps and limiting the introduction of infectious fluids to the patient preventing or reducing the likelihood of the patient acquiring the HAI.

17. The covers of claim 16, wherein the first and second covers are permanently closed on the first three edges and the second three edges.

18. The covers of claim 16, wherein the first cover is positionable to totally overlap the second cover when the first and second covers are attached by the third and loop fasteners and the sixth hook fasteners.

19. The covers of claim 16, wherein:
the third hook-and-loop fasteners extend most of the length between the first open end and a first closed end opposite to the first open end; and
the sixth hook-and-loop fasteners extend most of the length between the second open end and a second closed end opposite to the second open end.

20. The covers of claim 16, wherein the covers are separate when not attached by the third and sixth hook and loop material.

* * * * *